United States Patent
Mortimore et al.

(10) Patent No.: US 7,335,792 B2
(45) Date of Patent: Feb. 26, 2008

(54) PROCESS FOR SYNTHESIZING ASPARTIC AND GLUTAMIC ACID DERIVATIVES ESPECIALLY USEFUL AS INTERMEDIATES IN THE MANUFACTURE OF A CASPASE INHIBITOR

(75) Inventors: Michael Mortimore, Burford (GB); Oliver Philps, Abingdon (GB); John Studley, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 3 days.

(21) Appl. No.: 10/268,440

(22) Filed: Oct. 9, 2002

(65) Prior Publication Data

US 2003/0162993 A1   Aug. 28, 2003

Related U.S. Application Data

(60) Provisional application No. 60/328,065, filed on Oct. 9, 2001.

(51) Int. Cl.
*C07C 249/00* (2006.01)
*C07C 247/00* (2006.01)

(52) U.S. Cl. .......................................... 564/248; 552/6

(58) Field of Classification Search ..................... None
See application file for complete search history.

(56) References Cited

U.S. PATENT DOCUMENTS 5,756,466 A   5/1998   Bemis et al.

FOREIGN PATENT DOCUMENTS

GB   1 374 491    11/1974
JP   2000-290202  10/2000

OTHER PUBLICATIONS

Thornberry, *Chem. Biol.* 5:R-97-R103 (1998).
Chatterjee et al., *J. Med. Chem.* 40:3820-3828 (1997).
Nicholson, *Cell Death and Differentiation* 6:1028-1042 (1999).
Chéreau et al., *Biochemistry* 42:4151-4160 (2003).
Thornberry et al., *J. Biol. Chem.* 272:17907-17911 (1997).
Talanian et al., *J. Biol. Chem.* 272:9677-9682 (1997).
Garcia-Calvo et al., *J. Biol. Chem.* 273:32608-32613 (1998).
Graczyk, *Restorative Neurology and Neuroscience* 14:1-23 (1999).
Golec et al., *Bioorg. Med. Chem. Lett.* 7:2181-2186 (1997).
Dolle et al., *J. Med. Chem.* 39:2438-2440 (1996).
Alexander Golubev et al., "An Efficient Synthesis of 5-Hydroxy-4-oxo-L-norvaline from L-Aspartic acid", *Tet. Lett.*, 34, 5879-5880 (1993).

*Primary Examiner*—Karl Puttlitz
(74) *Attorney, Agent, or Firm*—Ropes & Gray LLP; James F. Haley, Jr.; David A. Roise

(57) ABSTRACT

The invention relates to novel diazoketone derivatives. The invention also relates to processes for homologation of these diazoketone derivatives. The processes are useful for preparing compounds that are caspase inhibitors.

8 Claims, No Drawings

PROCESS FOR SYNTHESIZING ASPARTIC AND GLUTAMIC ACID DERIVATIVES ESPECIALLY USEFUL AS INTERMEDIATES IN THE MANUFACTURE OF A CASPASE INHIBITOR

CROSS-REFERENCE TO RELATED APPLICATION

This application claims the benefit of U.S. Provisional Patent Application 60/328,065, filed Oct. 9, 2001.

TECHNICAL FIELD OF THE INVENTION

The invention relates to novel diazoketone derivatives. The invention also relates to processes for homologation of these diazoketone derivatives. The processes are useful for preparing compounds that are caspase inhibitors.

BACKGROUND OF THE INVENTION

Apoptosis, or programmed cell death, is a principal mechanism by which organisms eliminate unwanted cells. The deregulation of apoptosis, either excessive apoptosis or the failure to undergo it, has been implicated in a number of diseases such as cancer, acute inflammatory and autoimmune disorders, ischemic diseases and certain neurodegenerative disorders [see generally *Science*, 281, pp. 1283-1312 (1998); Ellis et al., *Ann. Rev. Cell. Biol.*, 7, p. 663 (1991)].

Caspases are a family of cysteine protease enzymes that are key mediators in the signaling pathways for apoptosis and cell disassembly [N. A. Thornberry, *Chem. Biol.*, 5, pp. R97-R103 (1998)]. These signaling pathways vary depending on cell type and stimulus, but all apoptosis pathways appear to converge at a common effector pathway leading to proteolysis of key proteins. Caspases are involved in both the effector phase of the signaling pathway and further upstream at its initiation. The upstream caspases involved in initiation events become activated and in turn activate other caspases that are involved in the later phases of apoptosis.

The utility of caspase inhibitors to treat a variety of mammalian disease states associated with an increase in cellular apoptosis has been demonstrated using peptidic caspase inhibitors. For example, in rodent models, caspase inhibitors have been shown to reduce infarct size and inhibit cardiomyocyte apoptosis after myocardial infarction, to reduce lesion volume and neurological deficit resulting from stroke, to reduce post-traumatic apoptosis and neurological deficit in traumatic brain injury, to be effective in treating fulminant liver destruction, and to improve survival after endotoxic shock [H. Yaoita et al., *Circulation*, 97, pp. 276-281 (1998); M. Endres et al., *J. Cerebral Blood Flow and Metabolism*, 18, pp. 238-247, (1998); Y. Cheng et al., *J. Clin. Invest.*, 101, pp. 1992-1999 (1998); A. G. Yakovlev et al., *J. Neurosci.*, 17, pp 7415-7424 (1997); I. Rodriquez et al., *J. Exp. Med.*, 184, pp. 2067-2072 (1996); Grobmyer et al., *Mol. Med.*, 5, p. 585 (1999)]. However, due to their peptidic nature, such inhibitors are typically characterized by undesirable pharmacological properties, such as poor cellular penetration and cellular activity, poor oral absorption, poor stability and rapid metabolism [J. J. Plattner and D. W. Norbeck, in *Drug Discovery Technologies*, C. R. Clark and W. H. Moos, Eds. (Ellis Horwood, Chichester, England, 1990), pp. 92-126]. This has hampered their development into effective drugs. These and other studies with peptidic caspase inhibitors have demonstrated that an aspartic acid residue is involved in a key interaction with the caspase enzyme [K. P. Wilson et al., *Nature*, 370, pp. 270-275 (1994); Lazebnik et al., *Nature*, 371, p. 346 (1994)].

Accordingly, non-peptidyl aspartic acid mimics are useful in the synthesis of caspase inhibitors. WO96/03982 reports azaaspartic acid analogs effective as interleukin-1β converting enzyme ("ICE") inhibitors. Fluoromethylketone analogs have also been reported as components of ICE inhibitors [WO99/47154; WO99/18781; WO93/05071].

It is well known that enzyme active sites are chiral and catalyze reactions stereospecifically. A substrate must fit precisely within this active site in order to interact with the enzyme. In accordance with this principle, a chiral compound could in many cases show improved inhibitory activity over its corresponding enantiomeric or diastereomeric mixtures.

Existing processes for synthesizing aspartic and glutamic acid derivatives and their analogues as caspase inhibitors or as intermediates for caspase inhibitors suffer from limited success and offer little control over stereochemistry [L. Revesz et al., *Tetrahedron Lett.*, 35, pp. 9693-9696 (1994); WO91/15577; D. Rasnick, *Anal. Biochem.*, 149, p.461 (1985)]. These transformations result in the formation of enantiomeric mixtures, which would require tedious separation steps to obtain an enantiomerically pure aspartic or glutamic acid mimic. Consequently, studies of the inhibitory activity of compounds with an aspartic or glutamic acid component generally refer to enantiomeric or diastereomeric mixtures, which may limit their effectiveness as enzyme inhibitors. Accordingly, the need exists for a process of synthesizing aspartic and glutamic acid analogues, and derivatives thereof, that are useful as intermediates for caspase inhibitors, to obtain chirally enriched derivatives in a reasonable yield.

Syntheses involving chiral diazoketones have been reported in the literature for the formation of β-amino-α-keto esters [Darkins et al., *Tetrahedron Assym.*, 5, pp. 195-198 (1994)], N-protected allylamine derivatives [Nishi et al., *Heterocycles*, 29, pp. 1835-1842 (1989)], and β-homoamino acids [Ondetti et al., *J. Med. Chem.*, 18, pp. 761-763 (1975)]. These procedures report little to no detectable racemization of the chiral center in the diazoketone transformation step.

SUMMARY OF THE INVENTION

The present invention solves the difficulties and shortcomings of the prior art for the synthesis of caspase inhibitors and provides chirally enriched aspartic and glutamic acid derivatives and processes for producing chirally enriched aspartic and glutamic acid derivatives. Applicants' approach to these aspartic and glutamic acid derivatives overcomes the problem of racemization of the chiral center adjacent to the amine, a problem sometimes encountered in existing methods of synthesizing aspartic and glutamic acid derivatives.

This invention solves the above problems by providing compounds of formula 1:

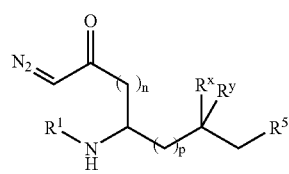

wherein $R^x$, $R^y$, $R^1$, $R^5$, n, and p are as described below. Compounds of formula 1 are useful as intermediates in the synthesis of aspartic and glutamic acid derivatives.

A process of this invention comprises the step of subjecting a diazoketone derivative of formula 1 to conditions that effect the rearrangement of 1 to form the corresponding homologation product 2:

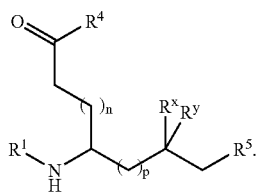

2

Homologation may be accomplished, for example, by reacting a compound of formula 1 in the presence of a base and a silver salt. Advantageously, this method preserves the chirality of the starting compound in the homologation product.

This process is particularly useful for producing caspase inhibitors and/or intermediates that may be subsequently converted into caspase inhibitors, through additional steps known in the art.

DETAILED DESCRIPTION OF THE INVENTION

Some of the abbreviations used through the specification (including the chemical formulae) are:

Bn=benzyl
Boc=t-butoxycarbonyl
Cbz=benzyloxycarbonyl
Alloc=allyloxycarbonyl
Ac=acetyl
TBDMS=t-butyldimethylsilyl
TBDPS=t-butyldiphenylsilyl
DMF=N,N-dimethylformamide
THF=tetrahydrofuran
DMSO=dimethylsulfoxide
PCC=pyridinium chlorochromate
PDC=pyridinium dichromate
TPAP=tetrapropylammonium perruthenate
THP=tetrahydropyranyl The present invention provides a process for homologating an α-amino acid derivative to the corresponding β-amino acid derivative whereby the asymmetry of the chiral center (*) is substantially preserved. This is shown in EQ. 1 where G represents the side chain of an α-amino acid:

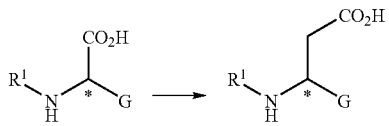

EQ. 1

The process is particularly useful for providing aspartic and glutamic acid derivatives wherein the carboxylic acid on the amino-bearing carbon is replaced by a substituted α-methyl ketone and $R^1$ is the P2-P4 portion of a caspase inhibitor. This is shown in EQ. 2 where $R^5$ is the substituent on the methyl ketone:

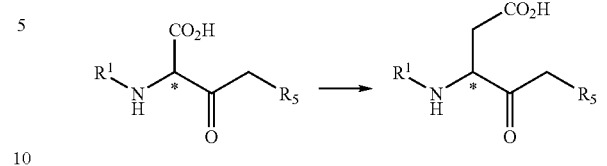

EQ. 2

Many α-amino acid derivatives of high optical purity are known in the literature and are useful starting materials for the current process. Since there is little or no racemization of the alpha carbon during the process of this invention, one may thereby obtain β-amino acid derivatives having an optical purity similar to that of the starting material.

The process is exemplified in the preparation of useful synthetic intermediates of caspase inhibitors:

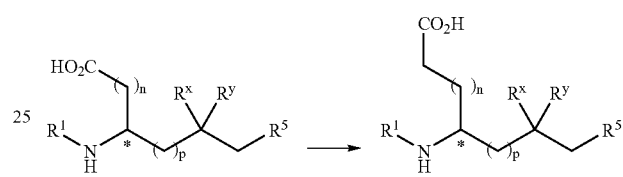

wherein $R^1$ is a P2-P4 portion of a caspase inhibitor; $R^x$ is H; $R^y$ is $OR^2$; $R^2$ is H or an alcohol protecting group; or $R^x$ and $R^y$ are taken together to form $—O(CH_2)_yO—$ or $=O$; y is 2-3; p is 0-6; and n is 0-6;

provided that when $R^x$ and $R^y$ are taken together to form $=O$, $R^1$ is other than H.

The symbol "*" denotes an asymmetric carbon. In a preferred embodiment of the present invention, the process provides compounds wherein one of the stereochemical forms of the asymmetric carbon is present in greater than about 50% excess over the other stereochemical form.

According to one embodiment, the invention provides a compound represented by formula 1:

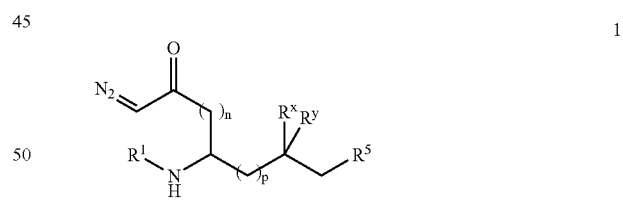

1 wherein:
$R^1$ is hydrogen; an amine protecting group; or a P2-P4 moiety of a caspase inhibitor, or portion thereof;
$R^x$ is H;
$R^y$ is $OR^2$;
or $R^x$ and $R^y$ are taken together to form $—O(CH_2)_yO—$ or $=O$; y is 2-3; provided that when $R^x$ and $R^y$ are taken together to form $=O$, $R^1$ is other than H;
each $R^2$ is independently hydrogen or an alcohol protecting group;
$R^5$ is an electronegative leaving group, halo, OR, or SR;
each R is independently hydrogen; C1-C6 aliphatic; or Ar;
wherein said aliphatic is optionally substituted with one or more substituents halo, C1-C6 alkoxy, cyano, nitro, oxo, $OR^2$, $OR^7$, $SR^7$, $N(R^6)_2$, $N(R^7)_2$, $N(R^6)(R^7)$, Ar, $Ar_1$, O—Ar, or O—$Ar_1$;

Ar is a saturated, partially saturated or unsaturated monocyclic or bicyclic ring structure, wherein each ring contains 5 to 7 ring atoms and each ring optionally contains from 1 to 4 heteroatoms selected from O, N and S;

wherein Ar is optionally substituted at one or more ring atoms with one or more substituents independently selected from halo; C1-C6 alkoxy; cyano; nitro; oxo; $OR^2$; $OR^7$; $SR^7$; $N(R^6)_2$; $N(R^7)_2$; $N(R^6)(R^7)$; $C(O)R^7$; $C(O)OR^7$; $C(O)N(R^7)_2$; $NR^7C(O)R^7$; $NR^7C(O)N(R^7)_2$; $NR^7SO_2R^7$; $SO_2N(R^7)_2$; $NR^7SO_2N(R^7)_2$; $Ar_1$; O—$Ar_1$; C1-C6 aliphatic optionally substituted with halo, C1-C6 alkoxy, cyano, nitro, oxo, $OR^2$, $OR^7$, $SR^7$, $N(R^6)_2$, $N(R^7)_2$, $N(R^6)(R^7)$; or O—C1-C6 aliphatic optionally substituted with halo, C1-C6 alkoxy, cyano, nitro, oxo, $OR^2$, $OR^7$, $SR^7$, $N(R^6)_2$, $N(R^7)_2$, $N(R^6)(R^7)$;

$Ar_1$ is a saturated, partially saturated or unsaturated monocyclic or bicyclic ring structure, wherein each ring contains 5 to 7 ring atoms and each ring optionally contains from 1 to 4 heteroatoms selected from O, N, and S;

each $R^6$ is independently hydrogen or an amine protecting group;

each $R^7$ is independently hydrogen; C1-C6 aliphatic optionally substituted with halo, C1-C6 alkoxy, cyano, nitro, amino, oxo or hydroxy; or a saturated, partially saturated or unsaturated monocyclic or bicyclic ring structure, wherein each ring contains 5 to 7 ring atoms and each ring optionally contains from 1 to 4 heteroatoms selected from O, N, and S, and wherein each ring atom is optionally substituted with 1 to 3 substituents independently selected from halo, C1-C6 alkyl, C1-C6 alkoxy, cyano, nitro, amino, and hydroxy;

n is 0-6; and p is 0-6.

According to a preferred embodiment, the compound of formula 1 is in greater than about 50% diastereomeric excess and greater than about 50% enantiomeric excess.

According to a more preferred embodiment, the compound of formula 1 is in greater than about 95% enantiomeric excess.

According to an even more preferred embodiment, the compound of formula 1 is in greater than about 98% enantiomeric excess.

According to a preferred embodiment, a compound of formula 1a or 1b:

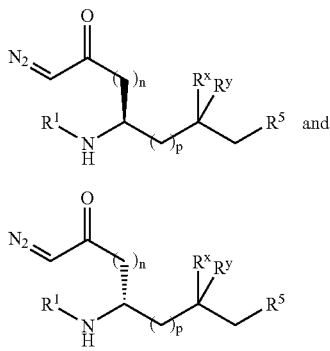

is provided.

According to one preferred embodiment, $R^1$ is a carbamate protecting group. More preferably, $R^1$ is Boc, Cbz, methyl carbamate, ethyl carbamate, 2,2,2-trichloroethyl carbamate, adamantyl carbamate, or Alloc.

In a more preferred embodiment, $R^1$ is Boc, Alloc, or Cbz. Most preferably, $R^1$ is Boc or Cbz.

According to another preferred embodiment, $R^1$ is a P2-P4 moiety of a caspase inhibitor, or portion thereof.

According to a preferred embodiment, $R^x$ is H and $R^y$ is $OR^2$.

In another preferred embodiment, $R^2$ is an ester or ether protecting group. More preferably, $R^2$ is formate, acetate, trichloroacetate, trifluoroacetate, phenylacetate, propionate, pivaloate, benzoate, substituted benzoate, benzyl, allyl, or tetrahydropyranyl.

In a most preferred embodiment, $R^2$ is acetate.

According to another preferred embodiment, $R^2$ is a silyl protecting group. More preferably, $R^2$ is trimethylsilyl, triethylsilyl, triisopropylsilyl, TBDMS, or TBDPS.

In a most preferred embodiment, $R^2$ is TBDMS.

According to another preferred embodiment, $R^5$ is F.

According to a preferred embodiment, $R^6$ is Boc, Cbz, alloc, trifluoroacetamide, or phthaloyl.

According to a preferred embodiment, n is 0 or 1. More preferably, n is 0.

According to a preferred embodiment, p is 0.

According to a more preferred embodiment, compound 1 is selected from the group consisting of:

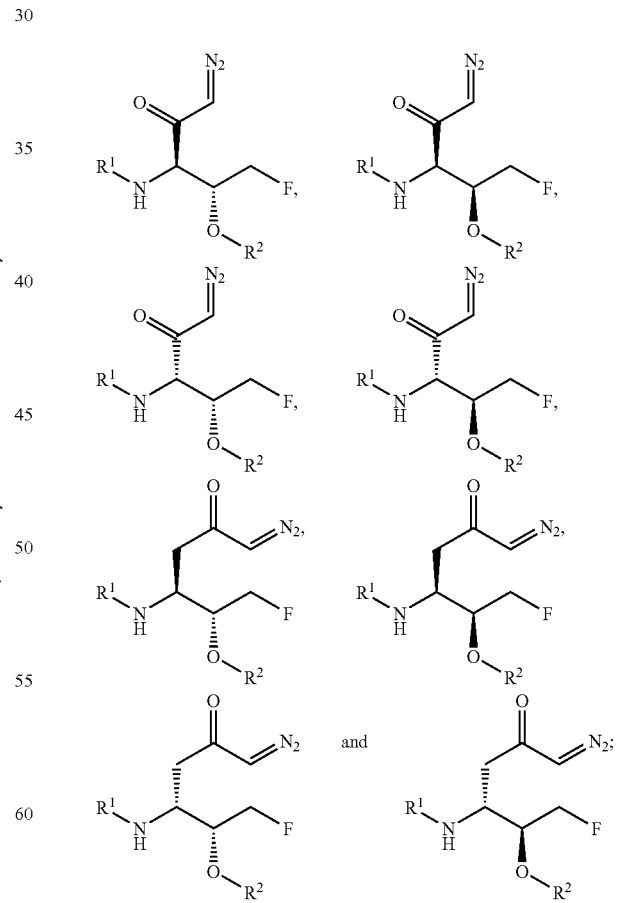

wherein $R^1$ and $R^2$ are as defined in any of the above embodiments.

According to a most preferred embodiment, compound 1 is selected from the group consisting of:

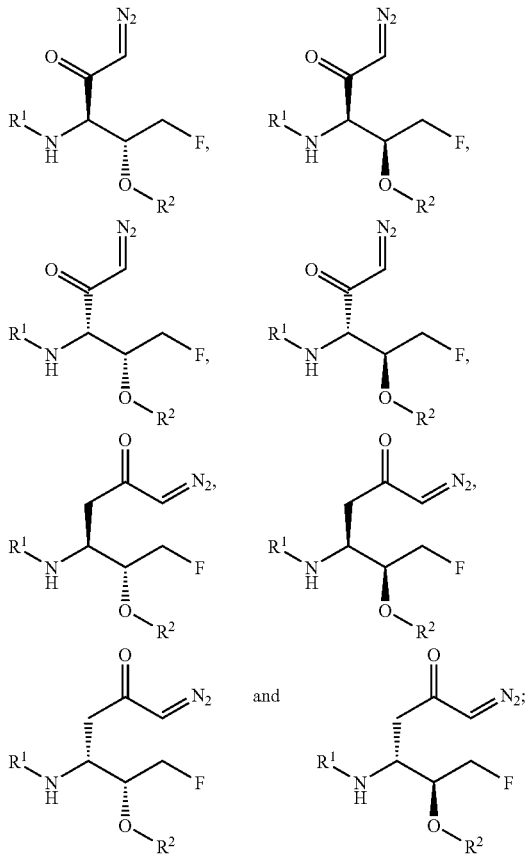

wherein $R^1$ is Boc, Cbz, or a P2-P4 moiety of a caspase inhibitor, or portion thereof; and $R^2$ is acetate or a silyl protecting group.

This invention also provides a process for converting compound 1 to compound 2:

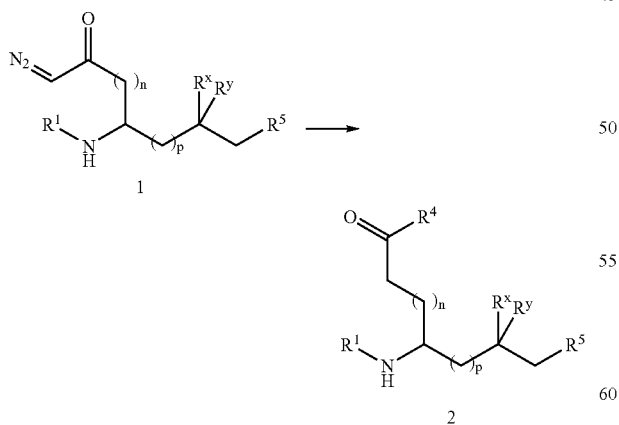

wherein:
$R^1$ is hydrogen; an amine protecting group; or a P2-P4 moiety of a caspase inhibitor, or portion thereof;
$R^x$ is H;
$R^y$ is $OR^2$;
or $R^x$ and $R^y$ are taken together to form $-O(CH_2)_yO-$ or $=O$; y is 2-3; provided that when $R^x$ and $R^y$ are taken together to form $=O$, $R^1$ is other than H;
each $R^2$ is independently hydrogen or an alcohol protecting group;
$R^4$ is OR, $OR^2$, $N(R)_2$, $N(R^6)_2$, $N(R^6)(R^7)$, or $N(R^7)_2$;
$R^5$ is an electronegative leaving group, halo, OR, or SR;
each R is independently hydrogen; C1-C6 aliphatic; or Ar; wherein said aliphatic is optionally substituted with one or more substituents halo, C1-C6 alkoxy, cyano, nitro, oxo, $OR^2$, $OR^7$, $SR^7$, $N(R^6)_2$, $N(R^7)_2$, $N(R^6)(R^7)$, Ar, $Ar_1$, O—Ar, or O—$Ar_1$;
Ar is a saturated, partially saturated or unsaturated monocyclic or bicyclic ring structure, wherein each ring contains 5 to 7 ring atoms and each ring optionally contains from 1 to 4 heteroatoms selected from O, N and S;
wherein Ar is optionally substituted at one or more ring atoms with one or more substituents independently selected from halo; C1-C6 alkoxy; cyano; nitro; oxo; $OR^2$; $OR^7$; $SR^7$; $N(R^6)_2$; $N(R^7)_2$; $N(R^6)(R^7)$; $C(O)R^7$; $C(O)OR^7$; $C(O)N(R^7)_2$; $NR^7C(O)R^7$; $NR^7C(O)N(R^7)_2$; $NR^7SO_2R^7$; $SO_2N(R^7)_2$; $NR^7SO_2N(R^7)_2$; $Ar_1$; O—$Ar_1$; C1-C6 aliphatic optionally substituted with halo, C1-C6 alkoxy, cyano, nitro, oxo, $OR^2$, $OR^7$, $SR^7$, $N(R^6)_2$, $N(R^7)_2$, $N(R^6)(R^7)$; or O—C1-C6 aliphatic optionally substituted with halo, C1-C6 alkoxy, cyano, nitro, oxo, $OR^2$, $OR^7$, $SR^7$, $N(R^6)_2$, $N(R^7)_2$, $N(R^6)(R^7)$;
$Ar_1$ is a saturated, partially saturated or unsaturated monocyclic or bicyclic ring structure, wherein each ring contains 5 to 7 ring atoms and each ring optionally contains from 1 to 4 heteroatoms selected from O, N, and S;
each $R^6$ is independently hydrogen or an amine protecting group;
each $R^7$ is independently hydrogen; C1-C6 aliphatic optionally substituted with halo, C1-C6 alkoxy, cyano, nitro, amino, oxo or hydroxy; or a saturated, partially saturated or unsaturated monocyclic or bicyclic ring structure, wherein each ring contains 5 to 7 ring atoms and each ring optionally contains from 1 to 4 heteroatoms selected from O, N, and S, and wherein each ring atom is optionally substituted with 1 to 3 substituents independently selected from halo, C1-C6 alkyl, C1-C6 alkoxy, cyano, nitro, amino, hydroxy;
n is 0-6; and
p is 0-6;
said process comprising the steps of:
providing a mixture of compound 1 and an organic solvent and subjecting the mixture to conditions that effect the rearrangement of compound 1 to compound 2.
In a preferred embodiment, said process comprises the steps of:
a) providing a mixture of compound 1 and an organic solvent;
b) adding to the mixture produced in step a):
i) a base; and
ii) a silver salt selected from $Ag_2O$ or $AgO_2CPh$; and
c) allowing the mixture produced in step b) to react at a temperature in the range of −50° C. and 150° C. for 1 minute to 48 hours to provide compound 2.
In another embodiment, a compound $R^4H$ is optionally added to the step a) mixture before step b).

Preferably, any of the processes according to this invention comprise the further step of purifying compound 2.

According to a preferred embodiment, $R^x$ is H and $R^y$ is $OR^2$.

Generally, the conversion of 1 to 2 will be performed under conditions in which $R^1$ is an amine protecting group or a P2-P4 moiety of a caspase inhibitor, or portion thereof, and $R^2$ is an alcohol protecting group.

According to a preferred embodiment, the compound of formula 2 is produced in greater than about 50% diastereomeric excess and greater than about 50% enantiomeric excess.

According to a more preferred embodiment, the compound of formula 2 is produced in greater than about 95% enantiomeric excess.

According to an even more preferred embodiment, the compound of formula 2 is produced in greater than about 98% enantiomeric excess.

According to a preferred embodiment, the compound of formula 1 is in greater than about 50% diastereomeric excess and greater than about 50% enantiomeric excess.

According to a more preferred embodiment, the compound of formula 1 is in greater than about 95% enantiomeric excess.

According to an even more preferred embodiment, the compound of formula 1 is in greater than about 98% enantiomeric excess.

According to a preferred embodiment, the process provides a compound of formula 2a or 2b:

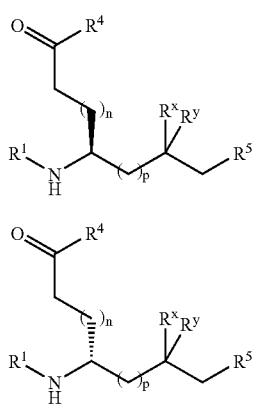

wherein $R^x$, $R^y$, $R^1$, $R^4$, $R^5$, n, and p are as above.

According to a preferred embodiment, $R^1$ is a P2-P4 moiety of a caspase inhibitor, or portion thereof.

According to a preferred embodiment, $R^1$ is a carbamate protecting group. More preferably, $R^1$ is Boc, Cbz, methyl carbamate, ethyl carbamate, 2,2,2-trichloroethyl carbamate, adamantyl carbamate, or Alloc.

In a more preferred embodiment, $R^1$ is Boc, Alloc, or Cbz.

Most preferably, $R^1$ is Boc or Cbz.

According to a preferred embodiment, $R^x$ is H and $R^y$ is $OR^2$.

In a more preferred embodiment, $R^2$ is an ester or ether protecting group. More preferably, $R^2$ is formate, acetate, trichloroacetate, trifluoroacetate, phenylacetate, propionate, pivaloate, benzoate, substituted benzoate, benzyl, allyl, or THP.

In a most preferred embodiment, $R^2$ is acetate.

According to another preferred embodiment, $R^2$ is a silyl protecting group. More preferably, $R^2$ is trimethylsilyl, triethylsilyl, triisopropylsilyl, TBDMS, or TBDPS.

In another most preferred embodiment, $R^2$ is TBDMS.

According to a preferred embodiment, $R^4$ is OR.

In a more preferred embodiment, R is $CH_3$, Bn, or t-butyl.

According to another preferred embodiment, $R^5$ is F.

According to a preferred embodiment, $R^6$ is Boc, Cbz, alloc, trifluoroacetamide, or phthaloyl.

According to a preferred embodiment, n is 0 or 1. In a more preferred embodiment, n is 0.

According to a preferred embodiment, p is 0.

According to a preferred embodiment, the organic solvent is a protic solvent.

In a more preferred embodiment, the organic solvent is methanol, t-butanol, isopropanol, benzyl alcohol or water.

Most preferably, the organic solvent is methanol, t-butanol, or benzyl alcohol.

When the process takes place in the presence of $R^4H$ wherein $R^4H$ is an alcohol, functionalized esters may be provided.

When the process takes place in the presence of ammonia or primary or secondary amines, primary, secondary, or tertiary amides, respectively, may be provided.

According to a preferred embodiment, the base is an aromatic or tertiary aliphatic amine. More preferably, the base is triethylamine, di-isopropylethylamine, N-methylmorpholine, pyrrolidine, pyridine or collidine.

According to a most preferred embodiment, the base is triethylamine.

According to another preferred embodiment, the silver salt is $AgO_2CPh$.

In another preferred embodiment, the mixture is allowed to react at a temperature in the range of 0° C. to room temperature.

In yet another preferred embodiment, the mixture is allowed to react for 1 to 24 hours.

Alternatively, according to another embodiment, compound 1 is converted to compound 2 by heating the mixture produced in step a), without the use of chemical reagents other than the organic solvent or $R^4H$.

According to yet another embodiment, compound 1 can be converted to compound 2 by exposing the mixture produced in step a) to UV light. Chemical reagents other than the organic solvent or $R^4H$ may optionally be present but are not required.

According to another embodiment, the invention provides a method for producing a compound of formula 3 from a compound of formula 1:

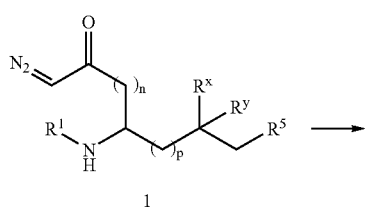

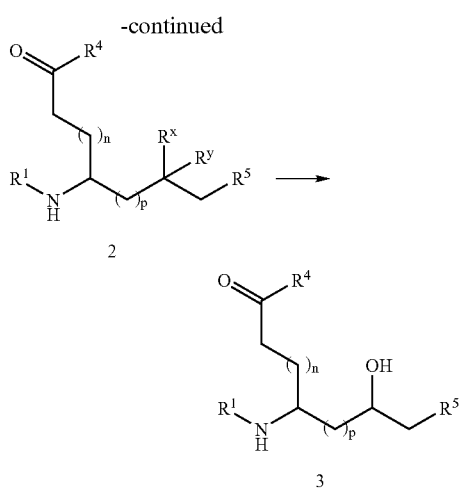

wherein:
R$^1$ is hydrogen; an amine protecting group; or a P2-P4 moiety of a caspase inhibitor, or portion thereof;
R$^x$ is H;
R$^y$ is OR$^2$;
or R$^x$ and R$^y$ are taken together to form —O(CH$_2$)$_y$O— or =O; y is 2-3; provided that when R$^x$ and R$^y$ are taken together to form =O, R$^1$ is other than H;
each R$^2$ is independently hydrogen or an alcohol protecting group;
R$^4$ is OR, OR$^2$, N(R)$_2$, N(R$^6$)$_2$, N(R$^6$)(R$^7$), or N(R$^7$)$_2$;
R$^5$ is an electronegative leaving group, halo, OR, or SR;
each R is independently hydrogen; C1-C6 aliphatic; or Ar; wherein said aliphatic is optionally substituted with one or more substituents halo, C1-C6 alkoxy, cyano, nitro, oxo, OR$^2$, OR$^7$, SR$^7$, N(R$^6$)$_2$, N(R$^7$)$_2$, N(R$^6$)(R$^7$), Ar, Ar$_1$, O—Ar, or O—Ar$_1$;
Ar is a saturated, partially saturated or unsaturated monocyclic or bicyclic ring structure, wherein each ring contains 5 to 7 ring atoms and each ring optionally contains from 1 to 4 heteroatoms selected from O, N and S;
wherein Ar is optionally substituted at one or more ring atoms with one or more substituents independently selected from halo; C1-C6 alkoxy; cyano; nitro; oxo; OR$^2$; OR$^7$; SR$^7$; N(R$^6$)$_2$; N(R$^7$)$_2$; N(R$^6$)(R$^7$); C(O)R$^7$; C(O)OR$^7$; C(O)N(R$^7$)$_2$; NR$^7$C(O)R$^7$; NR$^7$C(O)N(R$^7$)$_2$; NR$^7$SO$_2$R$^7$; SO$_2$N(R$^7$)$_2$; NR$^7$SO$_2$N(R$^7$)$_2$; Ar$_1$; O—Ar$_1$; C1-C6 aliphatic optionally substituted with halo, C1-C6 alkoxy, cyano, nitro, oxo, OR$^2$, OR$^7$, SR$^7$, N(R$^6$)$_2$, N(R$^7$)$_2$, N(R$^6$)(R$^7$); or O—C1-C6 aliphatic optionally substituted with halo, C1-C6 alkoxy, cyano, nitro, oxo, OR$^2$, OR$^7$, SR$^7$, N(R$^6$)$_2$, N(R$^7$)$_2$, N(R$^6$)(R$^7$);
Ar$_1$ is a saturated, partially saturated or unsaturated monocyclic or bicyclic ring structure, wherein each ring contains 5 to 7 ring atoms and each ring optionally contains from 1 to 4 heteroatoms selected from O, N, and S;
each R$^6$ is independently hydrogen or an amine protecting group;
each R$^7$ is independently hydrogen; C1-C6 aliphatic optionally substituted with halo, C1-C6 alkoxy, cyano, nitro, amino, oxo or hydroxy; or a saturated, partially saturated or unsaturated monocyclic or bicyclic ring structure, wherein each ring contains 5 to 7 ring atoms and each ring optionally contains from 1 to 4 heteroatoms selected from O, N, and S, and wherein each ring atom is optionally substituted with 1 to 3 substituents independently selected from halo, C1-C6 alkyl, C1-C6 alkoxy, cyano, nitro, amino or hydroxy;
n is 0-6; and
p is 0-6;
said process comprising the steps of:
a) converting compound 1 to compound 2;
b) wherein R$^x$ is H and R$^y$ is OR$^2$, and wherein R$^2$ is an alcohol protecting group, converting R$^2$ to hydrogen;
c) wherein R$^x$ and R$^y$ are taken together, optionally converting —C(R$^x$)(R$^y$)— to —CH(OH)—; and
d) wherein R$^1$ is an amine protecting group, converting R$^1$ to hydrogen.

One of skill in the art of will recognize that steps b) and d) or steps c) and d) can be performed in any order.

One of skill in the art will recognize that step c) may involve reducing the compound of formula 2, wherein R$^x$ and R$^y$ are taken together, to produce the free alcohol. This may involve, for example, subjecting the compound of formula 2 to a reducing agent.

In a preferred embodiment, the process further comprises the step of purifying compound 3.

According to a preferred embodiment, R$^x$ is H and R$^y$ is OR$^2$.

Generally, the conversion of 1 to 2 will be performed under conditions in which the amine and alcohol are protected, i.e., where R$^1$ is an amine protecting group or a P2-P4 moiety of a caspase inhibitor, or portion thereof and R$^2$ is an alcohol protecting group.

According to a preferred embodiment, the compound of formula 3 is produced in greater than about 50% diastereomeric excess and greater than about 50% enantiomeric excess.

According to a more preferred embodiment, the compound of formula 3 is produced in greater than about 95% enantiomeric excess.

According to an even more preferred embodiment, the compound of formula 3 is produced in greater than about 98% enantiomeric excess.

According to a preferred embodiment, the compound of formula 1 is in greater than about 50% diastereomeric excess and greater than about 50% enantiomeric excess.

According to a more preferred embodiment, the compound of formula 1 is in greater than about 95% enantiomeric excess.

According to an even more preferred embodiment, the compound of formula 1 is in greater than about 98% enantiomeric excess.

According to a preferred embodiment, the process provides a compound of formula 3a or 3b:

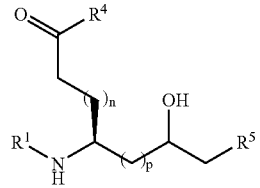

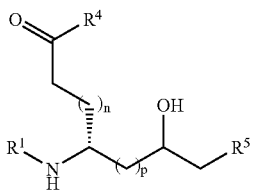

wherein $R^1$, $R^4$, $R^5$, n, and p are as above.

According to a preferred embodiment, $R^4$ is OR.

In a more preferred embodiment, R is H, $CH_3$, Bn, or t-butyl.

According to another preferred embodiment, $R^5$ is F.

According to a preferred embodiment, $R^6$ is Boc, Cbz, alloc, trifluoroacetamide, or phthaloyl.

According to a preferred embodiment, n is 0 or 1. In a more preferred embodiment, n is 0.

According to a preferred embodiment, p is 0.

According to another embodiment, the invention provides a method for producing a compound of formula 4 from a compound of formula 1:

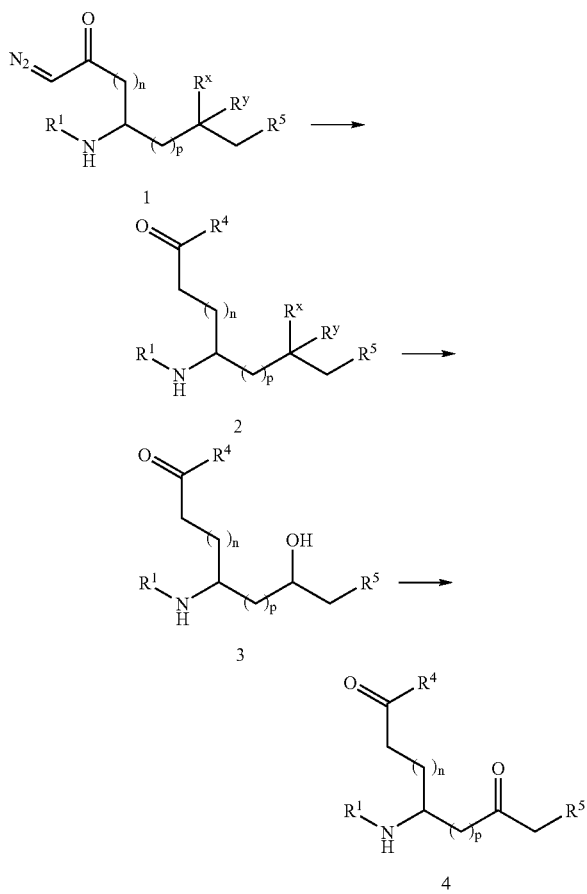

wherein:
$R^1$ is hydrogen; an amine protecting group; or a P2-P4 moiety of a caspase inhibitor, or portion thereof;
$R^x$ is H;
$R^y$ is $OR^2$;
or $R^x$ and $R^y$ are taken together to form —O(CH$_2$)$_y$O— or =O; y is 2-3; provided that when $R^x$ and $R^y$ are taken together to form =O, $R^1$ is other than H;
each $R^2$ is independently hydrogen or an alcohol protecting group;
$R^4$ is OR, $OR^2$, $N(R)_2$, $N(R^6)_2$, $N(R^6)(R^7)$, or $N(R^7)_2$;
$R^5$ is an electronegative leaving group, halo, OR, or SR;
each R is independently hydrogen; C1-C6 aliphatic; or Ar; wherein said aliphatic is optionally substituted with one or more substituents halo, C1-C6 alkoxy, cyano, nitro, oxo, $OR^2$, $OR^7$, $SR^7$, $N(R^6)_2$, $N(R^7)_2$, $N(R^6)(R^7)$, Ar, $Ar_1$, O—Ar, or O—$Ar_1$;
Ar is a saturated, partially saturated or unsaturated monocyclic or bicyclic ring structure, wherein each ring contains 5 to 7 ring atoms and each ring optionally contains from 1 to 4 heteroatoms selected from O, N and S;
wherein Ar is optionally substituted at one or more ring atoms with one or more substituents independently selected from halo; C1-C6 alkoxy; cyano; nitro; oxo; $OR^2$; $OR^7$; $SR^7$; $N(R^6)_2$; $N(R^7)_2$; $N(R^6)(R^7)$; $C(O)R^7$; $C(O)OR^7$; $C(O)N(R^7)_2$; $NR^7C(O)R^7$; $NR^7C(O)N(R^7)_2$; $NR^7SO_2R^7$; $SO_2N(R^7)_2$; $NR^7SO_2N(R^7)_2$; $Ar_1$; O—$Ar_1$; C1-C6 aliphatic optionally substituted with halo, C1-C6 alkoxy, cyano, nitro, oxo, $OR^2$, $OR^7$, $SR^7$, $N(R^6)_2$, $N(R^7)_2$, $N(R^6)(R^7)$; or O—C1-C6 aliphatic optionally substituted with halo, C1-C6 alkoxy, cyano, nitro, oxo, $OR^2$, $OR^7$, $SR^7$, $N(R^6)_2$, $N(R^7)_2$, $N(R^6)(R^7)$;
$Ar_1$ is a saturated, partially saturated or unsaturated monocyclic or bicyclic ring structure, wherein each ring contains 5 to 7 ring atoms and each ring optionally contains from 1 to 4 heteroatoms selected from O, N, and S;
each $R^6$ is independently hydrogen or an amine protecting group;
each $R^7$ is independently hydrogen; C1-C6 aliphatic optionally substituted with halo, C1-C6 alkoxy, cyano, nitro, amino, oxo or hydroxy; or a saturated, partially saturated or unsaturated monocyclic or bicyclic ring structure, wherein each ring contains 5 to 7 ring atoms and each ring optionally contains from 1 to 4 heteroatoms selected from O, N, and S, and wherein each ring atom is optionally substituted with 1 to 3 substituents independently selected from halo, C1-C6 alkyl, C1-C6 alkoxy, cyano, nitro, amino or hydroxy;
n is 0-6; and
p is 0-6;
said process comprising the step of oxidizing compound 3 to provide compound 4.

In a preferred embodiment, said process comprises the steps of:
a) converting compound 1 to compound 2;
b) wherein $R^x$ is H and $R^y$ is $OR^2$, and wherein $R^2$ is an alcohol protecting group, converting $R^2$ to hydrogen;
c) adding to the step b) mixture an oxidizing agent; and
d) allowing the mixture produced in step c) to react at a temperature in the range of −78° C. and 150° C. for 1 minute to 48 hours.

In a preferred embodiment, the process further comprises the step of purifying compound 4.

According to a preferred embodiment, $R^x$ is H and $R^y$ is $OR^2$.

Generally, the conversion of 1 to 2 will be performed under conditions in which the amine and alcohol are protected, i.e., where $R^1$ is an amine protecting group or a P2-P4 moiety of a caspase inhibitor, or portion thereof and $R^2$ is an alcohol protecting group.

According to a preferred embodiment, the compound of formula 4 is produced in greater than about 50% diastereomeric excess and greater than about 50% enantiomeric excess.

According to a more preferred embodiment, the compound of formula 4 is produced in greater than about 95% enantiomeric excess.

According to an even more preferred embodiment, the compound of formula 4 is produced in greater than about 98% enantiomeric excess.

According to a preferred embodiment, the compound of formula 1 is in greater than about 50% diastereomeric excess and greater than about 50% enantiomeric excess.

According to a more preferred embodiment, the compound of formula 1 is in greater than about 95% enantiomeric excess.

According to an even more preferred embodiment, the compound of formula 1 is in greater than about 98% enantiomeric excess.

According to a preferred embodiment, the process provides a compound of formula 4a or 4b:

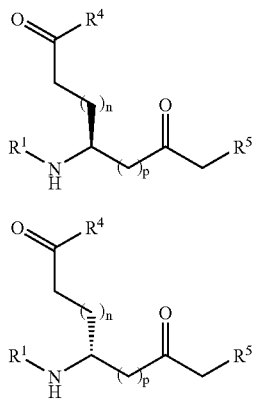

wherein $R^1$, $R^4$, $R^5$, n, and p are as above.

According to a preferred embodiment, $R^4$ is OR.

In a more preferred embodiment, R is H, $CH_3$, Bn, or t-butyl.

According to another preferred embodiment, $R^5$ is F.

According to a preferred embodiment, $R^6$ is Boc, Cbz, alloc, trifluoroacetamide, or phthaloyl.

According to a preferred embodiment, n is 0 or 1. In a more preferred embodiment, n is 0.

According to a preferred embodiment, p is 0.

According to a preferred embodiment, the oxidizing agent is Dess-Martin reagent, TPAP, DMSO/oxalyl chloride, or pyridine/$SO_3$.

In another preferred embodiment, the mixture produced in step c) is allowed to react at a temperature in the range of −78° C. and room temperature.

In yet another preferred embodiment, the mixture is allowed to react for 1 to 24 hours.

The synthesis of a compound of formula 1 is also within the scope of this invention. Accordingly, another embodiment of this invention provides a method for producing compound 1 from compound 11:

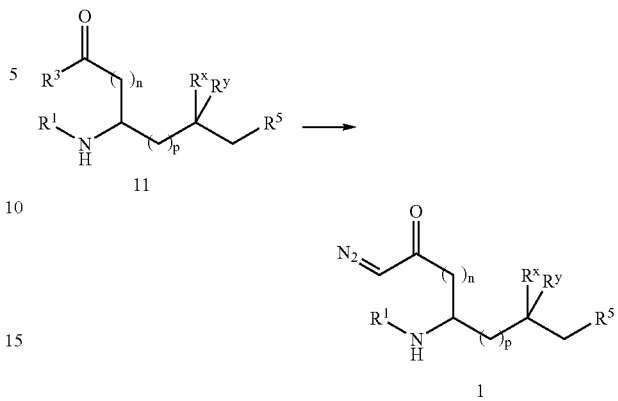

wherein:
$R^1$ is hydrogen; an amine protecting group; or a P2-P4 moiety of a caspase inhibitor, or portion thereof;
$R^x$ is H;
$R^y$ is $OR^2$;
or $R^x$ and $R^y$ are taken together to form —$O(CH_2)_yO$— or =O; y is 2-3; provided that when $R^x$ and $R^y$ are taken together to form =O, $R^1$ is other than H;
each $R^2$ is independently hydrogen or an alcohol protecting group;
$R^3$ is an acid activating group;
$R^5$ is an electronegative leaving group, halo, OR, or SR;
each R is independently hydrogen; C1-C6 aliphatic; and Ar; wherein said aliphatic is optionally substituted with one or more substituents halo, C1-C6 alkoxy, cyano, nitro, oxo, $OR^2$, $OR^7$, $SR^7$, $N(R^6)_2$, $N(R^7)_2$, $N(R^6)(R^7)$, Ar, $Ar_1$, O—Ar, or O—$Ar_1$;
Ar is a saturated, partially saturated or unsaturated monocyclic or bicyclic ring structure, wherein each ring contains 5 to 7 ring atoms and each ring optionally contains from 1 to 4 heteroatoms selected from O, N and S;
wherein Ar is optionally substituted at one or more ring atoms with one or more substituents independently selected from halo; C1-C6 alkoxy; cyano; nitro; oxo; $OR^2$; $OR^7$; $SR^7$; $N(R^6)_2$; $N(R^7)_2$; $N(R^6)(R^7)$; $C(O)R^7$; $C(O)OR^7$; $C(O)N(R^7)_2$; $NR^7C(O)R^7$; $NR^7C(O)N(R^7)_2$; $NR^7SO_2R^7$; $SO_2N(R^7)_2$; $NR^7SO_2N(R^7)_2$; $Ar_1$; O—$Ar_1$; C1-C6 aliphatic optionally substituted with halo, C1-C6 alkoxy, cyano, nitro, oxo, $OR^2$, $OR^7$, $SR^7$, $N(R^6)_2$, $N(R^7)_2$, $N(R^6)(R^7)$; or O—C1-C6 aliphatic optionally substituted with halo, C1-C6 alkoxy, cyano, nitro, oxo, $OR^2$, $OR^7$, $SR^7$, $N(R^6)_2$, $N(R^7)_2$, $N(R^6)(R^7)$;
$Ar_1$ is a saturated, partially saturated or unsaturated monocyclic or bicyclic ring structure, wherein each ring contains 5 to 7 ring atoms and each ring optionally contains from 1 to 4 heteroatoms selected from O, N, and S;
each $R^6$ is independently hydrogen or an amine protecting group;
each $R^7$ is independently hydrogen; C1-C6 aliphatic optionally substituted with halo, C1-C6 alkoxy, cyano, nitro, amino, oxo or hydroxy; or a saturated, partially saturated or unsaturated monocyclic or bicyclic ring structure, wherein each ring contains 5 to 7 ring atoms and each ring optionally contains from 1 to 4 heteroatoms selected from O, N, and S, and wherein each ring atom is optionally substituted with 1 to 3 substituents independently selected from halo, C1-C6 alkyl, C1-C6 alkoxy, cyano, nitro, amino or hydroxy;

n is 0-6; and p is 0-6;

said process comprising the step of converting compound 11 to compound 1.

One of skill in the art will recognize that converting compound 11 to compound 1 may involve subjecting compound 11 to conditions that will result in formation of the diazo derivative.

In a preferred embodiment, a method for producing compound 1 from compound 9 is provided:

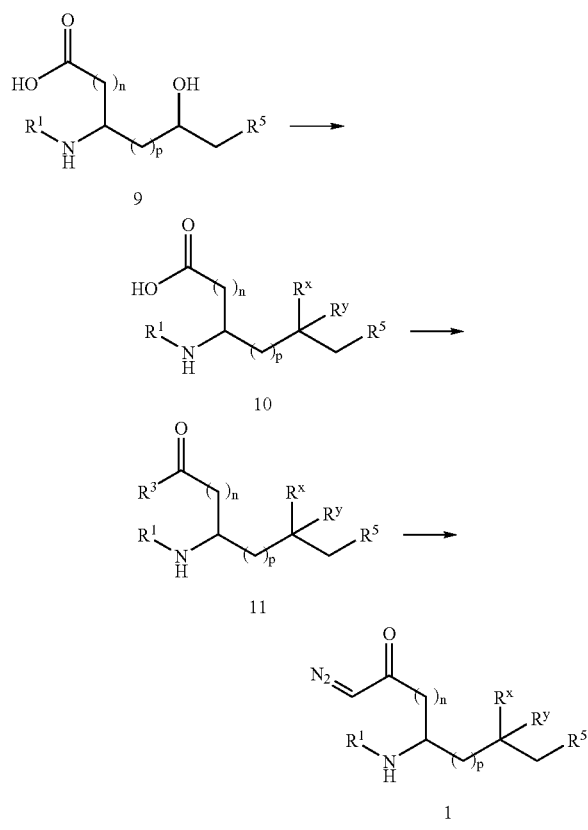

wherein:

$R^1$ is hydrogen; an amine protecting group; or a P2-P4 moiety of a caspase inhibitor, or portion thereof;

$R^x$ is H;

$R^y$ is $OR^2$;

or $R^x$ and $R^y$ are taken together to form —$O(CH_2)_yO$— or =O; y is 2-3; provided that when $R^x$ and $R^y$ are taken together to form =O, $R^1$ is other than H;

each $R^2$ is independently hydrogen or an alcohol protecting group;

$R^3$ is an acid activating group;

$R^5$ is an electronegative leaving group, halo, OR, or SR;

each R is independently hydrogen; C1-C6 aliphatic; or Ar; wherein said aliphatic is optionally substituted with halo, C1-C6 alkoxy, cyano, nitro, oxo, $OR^2$, $OR^7$, $SR^7$, $N(R^6)_2$, $N(R^7)_2$, $N(R^6)(R^7)$, Ar, $Ar_1$, O—Ar, or O—$Ar_1$;

Ar is a saturated, partially saturated or unsaturated monocyclic or bicyclic ring structure, wherein each ring contains 5 to 7 ring atoms and each ring optionally contains from 1 to 4 heteroatoms selected from O, N and S;

wherein Ar is optionally substituted at one or more ring atoms with one or more substituents independently selected from halo; C1-C6 alkoxy; cyano; nitro; oxo; $OR^2$; $OR^7$; $SR^7$; $N(R^6)_2$; $N(R^7)_2$; $N(R^6)(R^7)$; $C(O)R^7$; $C(O)OR^7$; $C(O)N(R^7)_2$; $NR^7C(O)R^7$; $NR^7C(O)N(R^7)_2$; $NR^7SO_2R^7$; $SO_2N(R^7)_2$; $NR^7SO_2N(R^7)_2$; $Ar_1$; O—$Ar_1$; C1-C6 aliphatic optionally substituted with halo, C1-C6 alkoxy, cyano, nitro, oxo, $OR^2$, $OR^7$, $SR^7$, $N(R^6)_2$, $N(R^7)_2$, $N(R^6)(R^7)$; or O—C1-C6 aliphatic optionally substituted with halo, C1-C6 alkoxy, cyano, nitro, oxo, $OR^2$, $OR^7$, $SR^7$, $N(R^6)_2$, $N(R^7)_2$, $N(R^6)(R^7)$;

$Ar_1$ is a saturated, partially saturated or unsaturated monocyclic or bicyclic ring structure, wherein each ring contains 5 to 7 ring atoms and each ring optionally contains from 1 to 4 heteroatoms selected from O, N, and S;

each $R^6$ is independently hydrogen or an amine protecting group;

each $R^7$ is independently hydrogen; C1-C6 aliphatic optionally substituted with halo, C1-C6 alkoxy, cyano, nitro, amino, oxo or hydroxy; or a saturated, partially saturated or unsaturated monocyclic or bicyclic ring structure, wherein each ring contains 5 to 7 ring atoms and each ring optionally contains from 1 to 4 heteroatoms selected from O, N, and S, and wherein each ring atom is optionally substituted with 1 to 3 substituents independently selected from halo, C1-C6 alkyl, C1-C6 alkoxy, cyano, nitro, amino or hydroxy;

n is 0-6; and p is 0-6;

said process comprising the steps of:

a) wherein $R^1$ is H, converting H to an amine protecting group;

b) converting the free alcohol to —$C(R^x)(R^y)$—;

c) activating the carboxylic acid;

d) converting the activated carboxylic acid formed in step c) to the corresponding diazoketone.

One of skill in the art will recognize that steps a) and b) can be performed in any sequence.

According to a preferred embodiment, $R^x$ is H and $R^y$ is $OR^2$. According to another preferred embodiment, $R^2$ is an alcohol protecting group.

Generally, the manipulative steps involved in the production of 1 will be performed under conditions in which the amine and alcohol are protected, i.e., where $R^1$ is an amine protecting group or a P2-P4 moiety of a caspase inhibitor, or portion thereof and $R^2$ is an alcohol protecting group.

Compounds of formula 9 may contain one or more chiral centers. These compounds may be obtained from commercial sources, or may be obtained by literature methods or modifications thereof that would be known to one of skill in the art. For example, in a preferred embodiment, the compound 9 may be the fluorothreonine 101:

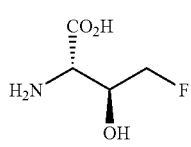

or another optically enriched amino acid derivative obtained through procedures known in the art. The high optical purity of these compounds may be achieved via the use of lipases [Shimizu et al., *Tet. Asymm.*, 4, pp. 835-838 (1993)] or an enantioselective synthesis that takes advantage of a configurationally stable cyclic intermediate [Amin et al., *Chem. Commun.*, 15, pp. 1471-1472 (1997); Scholastico et al., *Synthesis*, 9, pp. 850-855 (1985)]. Optical purity of the compound of formula 9 may be determined by analyzing the optical rotation, $^1$H NMR, $^{19}$F NMR, GC, HPLC, or other relevant property of the compound.

According to a preferred embodiment, the compound of formula 1 is produced in greater than about 50% diastereomeric excess and greater than about 50% enantiomeric excess.

According to a more preferred embodiment, the compound of formula 1 is produced in greater than about 95% enantiomeric excess.

According to an even more preferred embodiment, the compound of formula 1 is produced in greater than about 98% enantiomeric excess.

According to a preferred embodiment, the compound of formula 11 is in greater than about 50% diastereomeric excess and greater than about 50% enantiomeric excess.

According to a more preferred embodiment, the compound of formula 11 is in greater than about 95% enantiomeric excess.

According to an even more preferred embodiment, the compound of formula 11 is in greater than about 98% enantiomeric excess.

According to a preferred embodiment, the process provides a compound of formula 1a or 1b:

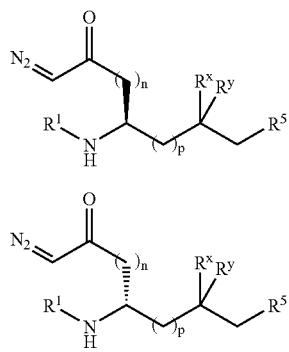

wherein $R^x$, $R^y$, $R^1$, $R^5$, n, and p are as above.

According to a preferred embodiment, $R^1$ is a P2-P4 moiety of a caspase inhibitor, or portion thereof.

According to a preferred embodiment, $R^1$ is a carbamate protecting group. More preferably, $R^1$ is Boc, Cbz, methyl carbamate, ethyl carbamate, 2,2,2-trichloroethyl carbamate, adamantyl carbamate, or Alloc.

In a more preferred embodiment, $R^1$ is Boc, Alloc, or Cbz. Most preferably, $R^1$ is Boc or Cbz.

According to a preferred embodiment, $R^x$ is H and $R^y$ is $OR^2$.

In a more preferred embodiment, $R^2$ is an ester or ether protecting group. More preferably, $R^2$ is formate, acetate, trichloroacetate, trifluoroacetate, phenylacetate, propionate, pivaloate, benzoate, substituted benzoate, benzyl, allyl, or THP.

In a most preferred embodiment, $R^2$ is acetate.

According to another preferred embodiment, $R^2$ is a silyl protecting group. More preferably, $R^2$ is trimethylsilyl, triethylsilyl, triisopropylsilyl, TBDMS, or TBDPS.

In another most preferred embodiment, $R^2$ is TBDMS.

According to another preferred embodiment, $R^3$ is Br, Cl, $OC(O)OCH_2CH(CH_3)_2$, $OC(O)OCH_2CH_3$, $OC(O)OCH_3$ or Cbz.

According to another preferred embodiment, $R^5$ is F.

According to a preferred embodiment, $R^6$ is Boc, Cbz, alloc, trifluoroacetamide, or phthaloyl.

According to a preferred embodiment, n is 0 or 1. In a more preferred embodiment, n is 0.

According to a preferred embodiment, p is 0.

According to a preferred embodiment, compound 11 is reacted with diazomethane or trimethylsilyldiazomethane to form the diazoketone 1.

As used herein, the following definitions shall apply unless otherwise indicated. Also, combinations of substituents are permissible only if such combinations result in stable compounds.

The term "aliphatic" as used herein means straight-chain, branched or cyclic hydrocarbons which are completely saturated or which contain one or more units of unsaturation. Preferred aliphatic groups have 1-12 carbon atoms. For example, suitable aliphatic groups include substituted or unsubstituted linear, branched, or cyclic alkyl, alkenyl, alkynyl groups and hybrids thereof such as (cycloalkyl)alkyl, (cycloaklenyl)alkyl or (cycloalkyl)alkenyl. The terms "alkyl" and "alkoxy" used alone or as part of a larger moiety refers to both straight and branched chains containing one to twelve carbon atoms. The terms "alkenyl" and "alkynyl" used alone or as part of a larger moiety shall include both straight and branched chains. Preferred alkenyl and alkynyl groups contain two to twelve carbon atoms. The term "halogen" or "halo" means F, Cl, Br, or I. The term "heteroatom" means N, O, or S and shall include any oxidized form of nitrogen and sulfur, and the quaternized form of any basic nitrogen.

In one embodiment of this invention is provided a process that may be used to prepare α-substituted methyl ketone aspartic acid and glutamic acid derivatives. Examples of such compounds include caspase inhibitors. Caspase inhibitors have been described in, for example, PCT patent publications WO 99/47545, WO 99/46248, WO 98/24805, WO 98/24804, WO 97/22619, WO 95/35308, WO 91/15577, WO 93/05071, WO 95/33751, WO 96/03982, WO 95/26958, and WO 95/29672, and European patent publications EP 623606, EP 644197, EP 628550, EP 644198, EP 623592, which are hereby incorporated by reference. Examples of caspase inhibitors include, without limitation:

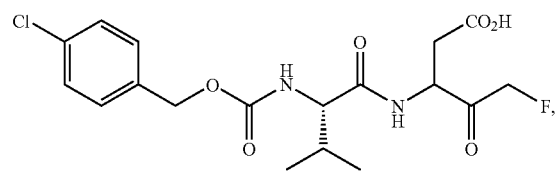

see, WO 00/61542

-continued

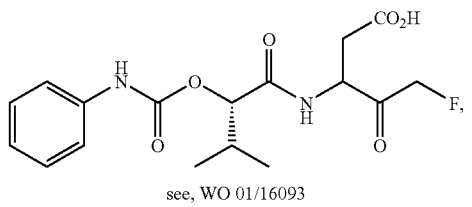

see, WO 01/16093

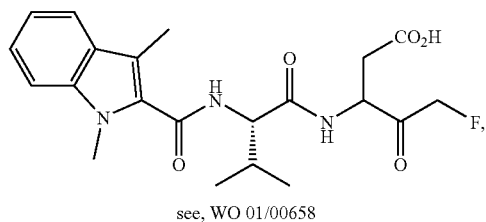

see, WO 01/00658

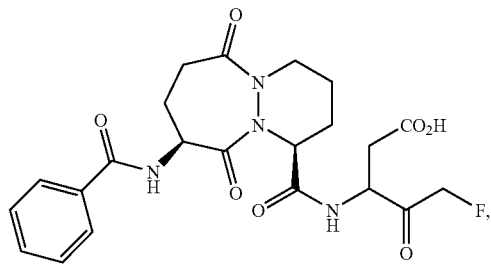

see, WO 97/22619

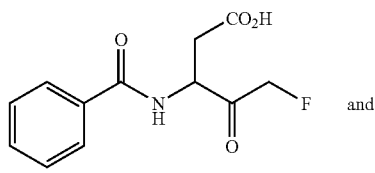

and see, WO 01/10383

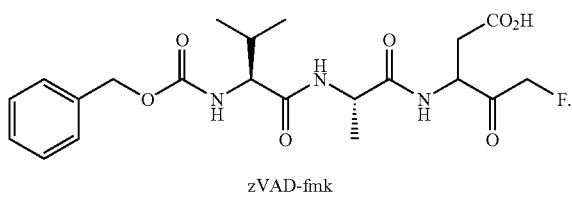

zVAD-fmk

The term "P2-P4 moiety of a caspase inhibitor, or portion thereof" as used herein, refers to a portion of a caspase inhibitor that is bound to an aspartic acid or aspartic acid derivative residue. For example, in the following caspase inhibitor:

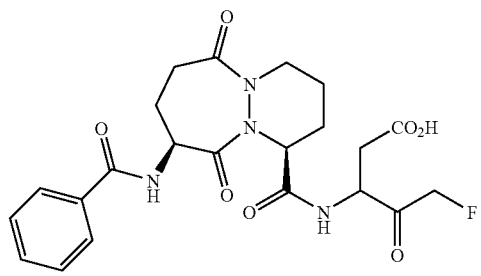

the P2-P4 moiety is:

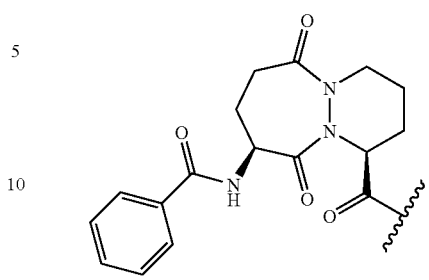

A portion of a P2-P4 moiety of a caspase inhibitor is a derivative or precursor thereof.

A derivative of a P2-P4 moiety of a caspase inhibitor is a P2-P4 moiety that has been modified in some way. As an example, for the above P2-P4 moiety, a structure such as:

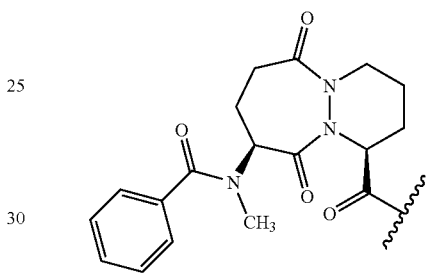

may be a derivative of a P2-P4 moiety of a caspase inhibitor. A precursor of a P2-P4 moiety is a compound useful as an intermediate in the synthesis of a caspase inhibitor or P2-P4 moiety of a caspase inhibitor. Again considering the above-listed WO 97/22619 example, a compound such as:

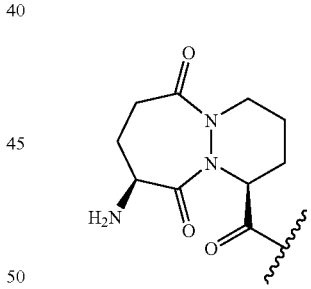

may be a precursor of the P2-P4 moiety of the caspase inhibitor.

Portions of a P2-P4 moiety of a caspase inhibitor are specifically referred to in the art as a P2, P3, or P4 moiety or site. These Px terms are references to the amino acid sequence next to the aspartyl cleavage site of a particular caspase substrate. P1 refers to the aspartyl residue of the substrate where caspase-induced cleavage occurs in the natural substrate. In the design of new, nonpeptidic caspase inhibitors, the Px designation is often retained to show which portion of the amino acid sequence has been replaced by the non-peptidic moiety. As used herein, the term "P2-P4" moiety refers to either the amino acid sequence described above or a chemical moiety known to replace such a sequence described above or a chemical moiety known to replace such a sequence for the purpose of being a caspase substrate, and in particular an ICE substrate.

Examples of P2-P4 moieties that are non-peptidic are described in U.S. Pat. No. 5,919,790 (Allen et al.); U.S. Pat. No. 5,874,424 (Batchelor et al.); U.S. Pat. No. 5,847,135 (Bemis et al.); U.S. Pat. No. 5,843,904 (Bemis et al.); U.S. Pat. No. 5,756,466 (Bemis et al.); U.S. Pat. No. 5,716,929 (Bemis et al.); U.S. Pat. No. 5,656,627 (Bemis et al.); WO 99/36426 (Warner-Lambert); Dolle et al., *J. Med. Chem.*, 40, 1941 (1997); WO 98/10778 (Idun); WO 98/11109 (Idun); WO 98/11129 (Idun) and WO 98/16502 (Warner Lambert), all of which are incorporated by reference.

The term "acid activating group", as used herein, has the definition known to those skilled in the art (see, March, *Advanced Organic Chemistry*, 4$^{th}$ Edition, John Wiley & Sons, 1992). Examples of acid activating groups include, without limitation, halogens such as F, Cl, Br, and I, mixed anhydrides, and imidazole.

The term "electronegative leaving group", as used herein, has the definition known to those skilled in the art (see, March, *Advanced Organic Chemistry*, 4$^{th}$ Edition, John Wiley & Sons, 1992). Examples of electronegative leaving groups include, without limitation, halogens such as F, Cl, Br, and I, aryl- and alkyl-sulfonyloxy groups, and trifluoromethanesulfonyloxy.

The term "organic solvent", as used herein, means any suitable solvent which may be readily selected by one of skill in the art. An organic solvent may be present in any quantity needed to facilitate the desired reaction, and does not necessarily have to dissolve the substrates and/or reagents of the desired reaction. Suitable organic solvents include, without limitation, halogenated solvents, hydrocarbon solvents, ether solvents, protic solvents, and aprotic solvents. Examples of suitable solvents include, without limitation, diethyl ether, THF, 1,4-dioxane, $CH_2Cl_2$, toluene, benzene, and DMF. Examples of protic solvents include, without limitation, methanol, t-butanol, isopropanol, benzyl alcohol and water. Mixtures of solvents are also included within the scope of this invention.

The term "base", as used herein, means any organic or inorganic base. Suitable bases may be readily selected by one of skill in the art of organic synthesis.

The term "amine protecting group", as used herein, means a moiety that temporarily blocks an amine reactive site in a compound. Generally, this is done so that a chemical reaction can be carried out selectively at another reactive site in a multifunctional compound or to otherwise stabilize the amine. An amine protecting group is preferably selectively removable by a chemical reaction. An amine protecting groups may be a carbamate protecting group. Carbamate protecting groups include, without limitation, Boc, Cbz, methyl carbamate, ethyl carbamate, 2,2,2-trichloroethyl carbamate, adamantyl carbamate, and Alloc.

The term "alcohol protecting group", as used herein, means a moiety that temporarily blocks an alcohol reactive site in a compound. Generally, this is done so that a chemical reaction can be carried out selectively at another reactive site in a multifunctional compound or to otherwise stabilize the alcohol. An alcohol protecting group is preferably selectively removable by a chemical reaction. An alcohol protecting group may be an ester protecting group. Ester alcohol protecting groups include, without limitation, formate, acetate, trichloroacetate, trifluoroacetate, phenylacetate, propionate, pivaloate, benzoate and substituted benzoate. An alcohol protecting group may also be a silyl protecting group. Silyl alcohol protecting groups include, without limitation, trimethylsilyl, triethylsilyl, triisopropylsilyl, t-butyldimethylsilyl, and t-butyldiphenylsilyl.

The term "oxidizing agent", as used herein, means any reagent or set of reagents capable of bringing about an oxidation reaction. These reagents are commonly known to one of skill in the art and include, without limitation, Dess-Martin reagent, DMSO/oxalyl chloride, TPAP, $SO_3$/pyridine, $CrO_3$/pyridine, Jones reagent, sodium dichromate, potassium dichromate, PCC, PDC, and sodium hypochlorite.

The term "reducing agent", as used herein, means any reagent or set of reagents capable of bringing about a reduction reaction. These reagents are commonly known to one of skill in the art and include, for example, $NaBH_4$, and may be selected with consideration of other functional groups present in the compound.

Unless otherwise stated, structures that are depicted without specifying a particular chirality are meant to include all stereochemical forms of the structure; i.e., the R and S configurations for each asymmetric center. Therefore, single stereochemical isomers as well as enantiomeric and diastereomeric mixtures of such compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium or the replacement of a carbon by a $^{13}$C- or $^{14}$C-enriched carbon are within the scope of this invention.

In order that this invention be more fully understood, the following examples are set forth. These examples are for the purpose of illustration only and are not to be construed as limiting the scope of the invention in any way.

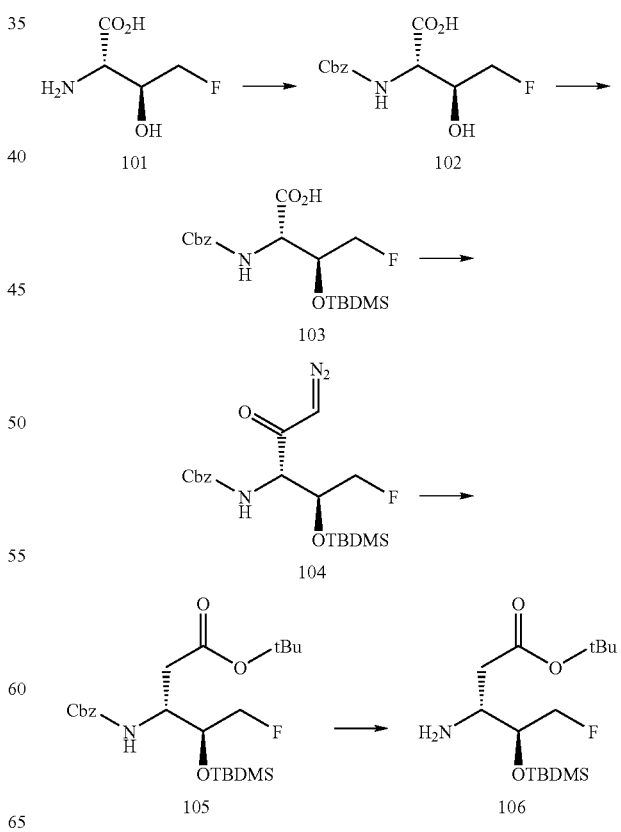

Scheme 1

EXAMPLE 1

N-Carboxybenzyloxy-(2S,3S)-4-fluorothreonine (102)

To a stirred solution of (2S,3S)-4-fluorothreonine 101 (0.100 g, 0.82 mmol) in THF/$H_2O$ (1:1, 5 ml) adjusted to pH 9 using sodium carbonate was added N-carboxybenzyloxysuccinimide (0.308 g, 1.24 mmol). After stirring the solution for 18 hours at room temperature, the solvent was removed in vacuo to give a white residue. The residue was partitioned between ethyl acetate (5 ml) and water (10 ml). The organic layer was separated and aqueous layer further extracted with ethyl acetate (2×5 ml), this organic phase was discarded. The pH of the aqueous layer was adjusted to 3 using 1N HCl. The aqueous layer was extracted with ethyl acetate (4×10 ml), the combined organic layers were dried ($MgSO_4$) and the solvent removed in vacuo to afford N-carboxybenzyloxy-(2S,3S)-4-fluorothreonine 102 as a pale yellow oil (110 mg, 70% yield); $^1H$ (400 MHz, $CDCl_3$) 8.20 (1H, bs, OH, exchange with $CH_3OD$), 6.46, 6.45 and 6.07 (1H, 3×d, J 8.9), 5.10-4.85 (2H, m, $CH_2Ph$), 4.65-4.25 (4H, H-2, H-3 and 4-$CH_2$); $^{19}F$ (376 MHz, $CDCl_3$) −228.59 and −228.51 (2×dtJ 46,14 due to rotamers).

N-Carboxybenzyloxy-O-tert-butyldimethylsilyl-(2S,3S)-4-fluorothreonine (103)

To a stirred solution of N-carboxybenzyloxy-(2S,3S)-4-fluorothreonine 102 (0.060 g, 0.22 mmol) in DMF (3 ml) was added tert-butyldimethylsilyl chloride (0.073 g, 0.49 mmol) and imidazole (0.033 g, 0.49 mmol). The solution was gently heated at 80° C. for 18 hours. After allowing the solution to cool to room temperature, the solution was diluted with dichloromethane (15 ml) and washed with 1N HCl solution (3×10 ml). The organic layer was dried ($MgSO_4$) and the solvent was removed in vacuo to give a yellow oil. The residue was redissolved in a 1:1 THF/methanol solution (4 ml) and upon stirring 50% aqueous acetic acid (2 ml) was added. After stirring the solution vigorously for 4 hours the solvent was removed in vacuo to give a yellow oil. Trace amounts of acetic acid were removed by treatment of the residue in ethyl acetate (5 ml) with saturated sodium hydrogen carbonate solution (10 ml). The organic layer was dried ($MgSO_4$) and the solvent removed in vacuo to afford N-carboxybenzyloxy-O-tert-butyldimethylsilyl-(2S,3S)-4-fluorothreonine 103 as a pale yellow oil (0.073 g, 86% yield); $^1H$ (400 MHz, $CDCl_3$) 9.50 (1H, bs, OH, exchange with $CH_3OD$), 7.60-7.20 (5H, m, Ph), 6.25, 5.75 and 5.45 (1H, 3×d, J 9.1, NH, exchange with $CH_3OD$), 5.20-5.10 (2H, m, $CH_2Ph$), 4.75-4.20 (4H, H-2, H-3, 4-$CH_2$), 1.00-0.80 (9H, 2×s, $SiC(CH_3)_3$), 0.15-0.00 (6H, m, $Si(CH_3)_2$); $^{19}F$ (376 MHz, $CDCl_3$) −224.82 and −225.39 (2×dtJ 47, 4 due to rotamers).

N-Carboxybenzyloxy-O-tert-butyldimethylsilyl-(2S,3S)-4-fluorothreonine diazoketone (104)

To a stirred solution of N-carboxybenzyloxy-O-tert-butyldimethylsilyl-(2S,3S)-4-fluorothreonine 103 (0.450 g, 1.17 mmol) in THF (12 ml) at 0° C. was added N-methylmorpholine (0.192 ml, 1.75 mmol) and isobutyl chloroformate (0.212 ml, 1.63 mmol). After stirring the suspension for 15 minutes, diethyl ether (20 ml) was added. The suspension was filtered and the filtrate reacted with diazomethane (4.90 mmol, prepared from Diazald) at 0° C. After allowing the solution to stand overnight, the solvent was removed in vacuo to give a pale yellow residue. Purification by column chromatograpy (3:1 petroleum ether 60-80° C./ethyl acetate) afforded N-carboxybenzyloxy-O-tert-butyldimethylsilyl-(2S,3S)-4-fluorothreonine diazoketone 104 as a pale yellow solid (0.277 g, 58% yield); Rf 0.48 (3:1 petroleum ether 60-80° C./ethyl acetate, UV light); $^1H$ (400 MHz, $CDCl_3$) 7.60-7.30 (5H, m, Ph), 5.85-5.65 (2H, m, $CHN_2$, NH exchangeable with $CH_3OD$), 5.20-5.10 (2H, m, $CH_2Ph$), 4.70-4.20 (4H, H-2, H-3, 4-$CH_2$), 0.87 (9H, s, $SiC(CH_3)_3$), 0.15-0.00 (6H, m, $Si(CH_3)_2$); $^{19}F$ (376 MHz, $CDCl_3$) −225.28 and −226.02 (2×dtJ 47,14, due to rotamers).

tert-Butyl N-(3S)-carboxybenzyloxy-O-(4S)-tert-butyldimethylsilyl-5-fluoropentanoate (105)

To a stirred solution of N-carboxybenzyloxy-O-tert-butyldimethylsilyl-(2S,3S)-4-fluorothreonine diazoketone 104 (0.277 g, 0.68 mmol) in tert-butanol (10 ml) was added a solution of silver benzoate (15 mg, 0.068 mmol) in triethylamine (0.094 ml, 0.68 mmol). After stirring for 18 hours at room temperature the suspension was filtered through Celite. The solvent of the filtrate was removed in vacuo to give a brown residue. The residue was redissolved in diethyl ether (15 ml) and washed with saturated sodium hydrogen carbonate solution (2×15 ml). The organic layer was dried ($MgSO_4$) and the solvent removed in vacuo to give a yellow oil. Purification by column chromatograpy (6:1 petroleum ether 60-80° C./ethyl acetate) gave tert-butyl N-(3S)-carboxybenzyloxy-O-(4S)-tert-butyldimethylsilyl-5-fluoropentanoate 105 as a pale yellow oil (0.166 g, 54% yield); Rf 0.59 (6:1 petroleum ether 60-80° C./ethyl acetate, ninhydrin stain); $^1H$ (400 MHz, $CDCl_3$) 7.50-7.30 (5H, m, Ph), 5.40-5.05 (3H, $CH_2Ph$, NH), 4.55-3.95 (4H, $CH_2F$, H-3, H-4), 2.50 (2H, d, J 7.2, 2-$CH_2$), 1.43 (9H, s, $CO_2(CH_3)_3$), 0.91 (9H, s, $SiC(CH_3)_3$), 0.10 (6H, m, $Si(CH_3)_2$); $^{19}F$ (376 MHz, $CDCl_3$) −225.67 (dt, J 46, 16); $^{19}F$ (376 MHz, $CDCl_3$, decoupled) −225.58 and −225.67 (2×s due to rotamers).

tert-Butyl O-(4S)-tert-butyldimethylsilyl-5-fluoropentanoate (106)

To a stirred suspension of 10% palladium on carbon (2 mg, 10% w/w) in ethyl acetate (2 ml) was added tert-butyl N-(3S)-carboxybenzyloxy-O-(4S)-tert-butyldimethylsilyl-5-fluoropentanoate 105 (10 mg, 0.022 mmol) in ethyl acetate (2 ml). The flask was evacuated and put under an atmosphere of hydrogen. After stirring for four hours at room temperature the suspension was filtered through Celite. The solvent of the filtrate was removed in vacuo to give tert-butyl O-(4S)-tert-butyldimethylsilyl-5-fluoropentanoate 106 as a colourless oil (7 mg, 100% yield); $^1H$ (400 MHz, $CDCl_3$) 4.75-4.35 (2H, m, $CH_2F$), 4.32-3.85 (2H, H-3, H-4), 2.80-2.30 (2H, m, 2-$CH_2$), 1.46 (9H, s, $CO_2(CH_3)_3$), 0.91 (9H, s, $SiC(CH_3)_3$), 0.08 (6H, m, $Si(CH_3)_2$); $^{19}F$ (376 MHz, $CDCl_3$) −225.84 (dt, J 48, 14); $^{19}F$ (376 MHz, $CDCl_3$, decoupled) −225.84 (s).

While we have hereinbefore presented a number of embodiments of this invention, it is apparent that the basic construction can be altered to provide other embodiments which utilize the methods of this invention. Therefore, it will be appreciated that the scope of this invention is to be defined by the claims appended hereto rather than the specific embodiments which have been presented hereinbefore by way of example.

What is claimed is:

1. A compound represented by formula 1:

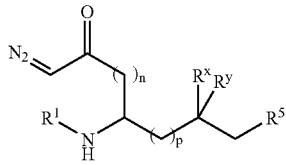

wherein:
R$^1$ is hydrogen; an amine protecting group; or a P2-P4 moiety of a caspase inhibitor, or portion thereof
R$^x$ is H;
R$^y$ is OR$^2$;
or R$^x$ and R$^y$ are taken together to form —O(CH$_2$)$_y$O— or =O; y is 2-3; provided that when R$^x$ and R$^y$ are taken together to form =O, R$^1$ is other than H;
each R$^2$ is independently hydrogen or an alcohol protecting group;
R$^5$ is an electronegative leaving group
n is 0-6; and
p is 0-6.

2. The compound according to claim 1, selected from:

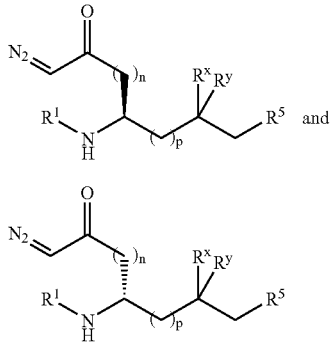

wherein R$^x$, R$^y$, R$^1$, R$^5$, n, and p are as defined in claim 1.

3. The compound according to claim 1, wherein R$^x$ is H and R$^y$ is OR$^2$; R$^5$ is F; n is 0 or 1; and p is 0.

4. The compound according to claim 1, selected from the group consisting of:

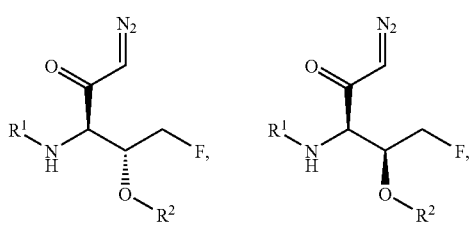

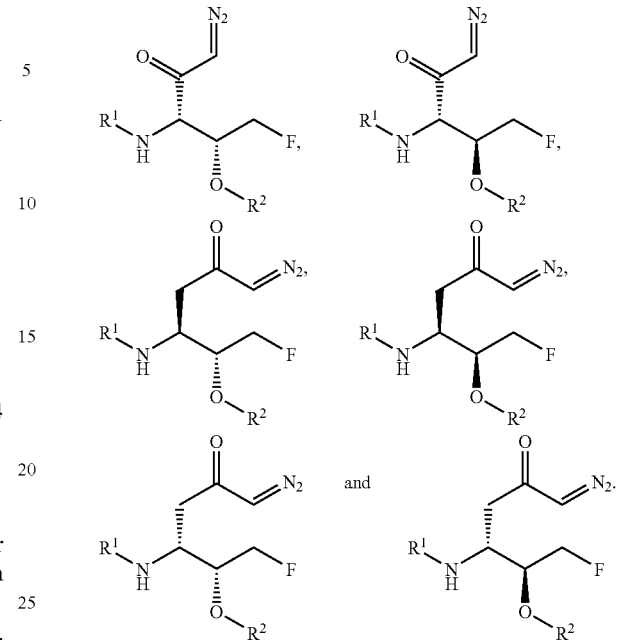

5. The compound according to claim 4, wherein:
R$^1$ is selected from the group consisting of Boc; Cbz; and a P2-P4 moiety of a caspase inhibitor, or portion thereof; and
R$^2$ is selected from the group consisting of acetate and a silyl protecting group.

6. A compound represented by formula 1:

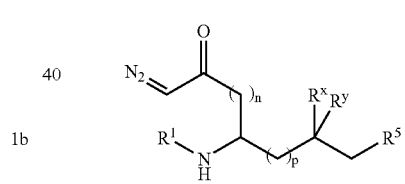

wherein:
R$^1$ is hydrogen; an amine protecting group; or a P2-P4 moiety of a caspase inhibitor, or portion thereof;
R$^x$ is H;
R$^y$ is OR$^2$;
or R$^x$ and R$^y$ are taken together to form —O(CH$_2$)$_y$O— or =O; y is 2-3; provided that when R$^x$ and R$^y$ are taken together to form =O, R$^1$ is other than H;
each R$^2$ is independently hydrogen or an alcohol protecting group;
R$^5$ is halo, OR, or SR;
each R is independently hydrogen; C1-C6 aliphatic; or Ar; wherein said aliphatic is optionally substituted with one or more substituents halo, C1-C6 alkoxy, cyano, nitro, oxo, OR$^2$, OR$^7$, SR$^7$, N(R$^6$)$_2$, N(R$^7$)$_2$, N(R$^6$)(R$^7$), Ar, Ar$_1$, O—Ar, or O—Ar$_1$;
Ar is a saturated, partially saturated or unsaturated monocyclic or bicyclic ring structure, wherein each ring contains 5 to 7 ring atoms and each ring optionally contains from 1 to 4 heteroatoms selected from O, N and S;

wherein Ar is optionally substituted at one or more ring atoms with one or more substituents independently selected from halo; C1-C6 alkoxy; cyano; nitro; oxo; $OR^2$; $OR^7$; $SR^7$; $N(R^6)_2$; $N(R^7)_2$; $N(R^6)(R^7)$; $C(O)R^7$; $C(O)OR^7$; $C(O)N(R^7)_2$; $NR^7C(O)R^7$; $NR^7C(O)N(R^7)_2$; $NR^7SO_2R^7$; $SO_2N(R^7)_2$; $NR^7SO_2N(R^7)_2$; $Ar_1$; O—$Ar_1$; C1-C6 aliphatic optionally substituted with halo, C1-C6 alkoxy, cyano, nitro, oxo, $OR^2$, $OR^7$, $SR^7$, $N(R^6)_2$, $N(R^7)_2$, or $N(R^6)(R^7)$; or O—C1-C6 aliphatic optionally substituted with halo, C1-C6 alkoxy, cyano, nitro, oxo, $OR^2$, $OR^7$, $SR^7$, $N(R^6)_2$, $N(R^7)_2$, or $N(R^6)(R^7)$;

$Ar_1$ is a saturated, partially saturated or unsaturated monocyclic or bicyclic ring structure, wherein each ring contains 5 to 7 ring atoms and each ring optionally contains from 1 to 4 heteroatoms selected from O, N, and S;

each $R^6$ is independently hydrogen or an amine protecting group;

each $R^7$ is independently hydrogen; C1-C6 aliphatic optionally substituted with halo, C1-C6 alkoxy, cyano, nitro, amino, oxo or hydroxy; or a saturated, partially saturated or unsaturated monocyclic or bicyclic ring structure, wherein each ring contains 5 to 7 ring atoms and each ring optionally contains from 1 to 4 heteroatoms selected from O, N, and S, and wherein each ring atom is optionally substituted with 1 to 3 substituents independently selected from halo, C1-C6 alkyl, C1-C6 alkoxy, cyano, nitro, amino, and hydroxy;

n is 0-6; and p is 0-6.

7. The compound according to claim 6, selected from:

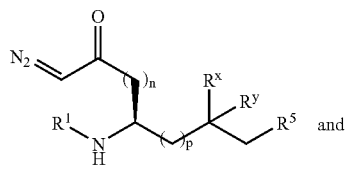

1a

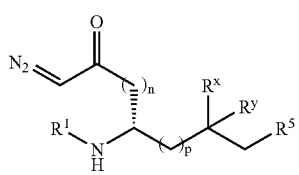

1b wherein $R^x$, $R^y$, $R^1$, $R^5$, n, and p are as defined in claim 6.

8. The compound according to claim 6, wherein $R^x$ is H and $R^y$ is $OR^2$; $R^5$ is halo; n is 0 or 1; and p is 0.

* * * * *